United States Patent [19]

Shiragami et al.

[11] Patent Number: 5,451,671
[45] Date of Patent: *Sep. 19, 1995

[54] METHOD OF PURIFYING 2',3'-DIDEOXYNUCLEOSIDES

[75] Inventors: Hiroshi Shiragami; Masayuki Arai; Kunisuke Izawa; Yutaka Honda; Yasuhiro Tanaka; Toshihide Yukawa, all of Kawasaki; Satoji Takahashi, Yokkaichi, all of Japan

[73] Assignee: Ajinomoto Co., Inc., Tokyo, Japan

[*] Notice: The portion of the term of this patent subsequent to Oct. 9, 2004 has been disclaimed.

[21] Appl. No.: 76,964

[22] Filed: Jun. 16, 1993

[30] Foreign Application Priority Data

Jul. 27, 1992 [JP] Japan .................. 4-199964
Jul. 27, 1992 [JP] Japan .................. 4-199965

[51] Int. Cl.$^6$ .................................. C07H 19/173
[52] U.S. Cl. .................. 536/27.12; 536/28.2; 536/27.14
[58] Field of Search .................. 536/27.12, 27.14

[56] References Cited

U.S. PATENT DOCUMENTS

| | | | |
|---|---|---|---|
| 3,817,982 | 6/1974 | Verheyden et al. | 536/27.14 |
| 4,835,104 | 5/1989 | Yokozeki et al. | 435/87 |
| 4,962,193 | 10/1990 | Yokozeki et al. | 536/27.12 |

FOREIGN PATENT DOCUMENTS

| | | | |
|---|---|---|---|
| 0199451 | 10/1986 | European Pat. Off. | 514/50 |
| 0217580 | 4/1987 | European Pat. Off. | 514/49 |
| 1098496 | 4/1989 | Japan | 536/27.14 |
| 1102095 | 4/1989 | Japan | 536/28.2 |
| 2204489 | 8/1990 | Japan | 536/27.14 |
| 2243690 | 9/1990 | Japan | 536/27.14 |
| 8904462 | 6/1989 | WIPO | 514/46 |

OTHER PUBLICATIONS

Honig et al. eds., *The Van Nostrand Chemist's Dictionary*, D. Van Nostrand Co. Inc., New York, N.Y., 1953, p. 620.

Budavari et al. eds., *The Merck Index, An Encyclopedia of Chemicals, Drugs, and Biologicals*, 11th Ed., Merck & Co, Inc., Rahway, N.J., 1989, entry numbers 3090, 141, 3092, 4805.

Acheson, *An Introduction to the Chemistry of Heterocyclic Compounds*, 2nd Ed., Interscience Publishers, New York, N.Y., 1967, p. 302, 354–355.

Japanese Laid-Open Application No: 1-198496, Apr. 17, 1989.

Japanese Laid-Open Application No: 1-175990, Jul. 12, 1989.

Japanese Laid-Open Application No: 1-165390, Jun. 29, 1989.

Japanese Laid-Open Application No: 1-175991, Jul. 12, 1989.

The Journal of Organic Chemistry, vol. 54, Sep. 29, 1989, No. 20, Mansuri et al, 43,4780.

Journal of Medicinal Chemistry, vol. 33, No. 6, Amrican Chemical Society, Chu et al. 33,1553.

Tetrahedron Letters, vol. 25, No. 4. pp. 367–370, (1984), Robins et al, 25,367.

Journal of the American Chemical Society, vol. 88, Apr. 5, 1966, No. 7, McCarthy et al, 88,1549.

*Primary Examiner*—Douglas W. Robinson
*Assistant Examiner*—L. Eric Crane
*Attorney, Agent, or Firm*—Oblon, Spivak, McClelland, Maier & Neustadt

[57] ABSTRACT

A crude 2',3'-dideoxynucleoside compound is purified by extracting with an organic solvent, or crystallizing, the 2',3'-dideoxynucleoside compound from a basic aqueous solution having a pH of not less than 12 containing the same. In another embodiment of purification a basic aqueous solution having a pH of not less than 11 of a crude 2',3'-dideoxynucleoside derivative is brought into contact with a nonpolar porous resin, whereby the derivative is adsorbed on the resin, and then the thus adsorbed derivative is desorbed with an aqueous alcoholic solution.

2',3'-Dideoxynucleoside compounds which have utility as anti-AIDS drugs or anti-virus drugs can be isolated and purified in high purity and in high yield from their crude products containing impurities.

8 Claims, 6 Drawing Sheets

METHOD OF PURIFYING 2',3'-DIDEOXYNUCLEOSIDES

BACKGROUND OF THE INVENTION

1. Field of the Invention

The present invention relates to a method of purifying dideoxynucleoside and, more particularly, 2',3'dideoxynucleoside-derivatives which have already been authorized or are under assessment as anti-AIDS drugs and anti-virus drugs. 2',3'-Dideoxyinosine (ddI), 2',3'-dideoxycytidine (ddC) and 3'-deoxy-3'-azidothymidine (AZT) have already been authorized as anti-AIDS drugs by the FDA (the Federal Food and Drug Administration).

2. Discussion of the Background

Several methods have been reported for the isolation and purification of 2',3'-dideoxynucleoside derivatives from crude reaction products. One method is purification by recrystallization from an organic solvent (McCarthy et al., J. Am. Chem. Soc., (1966) 88, 1549, Mansuri et al., J. Org. Chem., (1989) 43, 4780 and Robins et al., Tetrahedron Lett., (1984) 25, 367). Another method is purification by silica gel chromatography or by using synthetic adsorption resins (U.S. Pat. No. 3,817,982 and Chu et al., J. Med. Chem., (1990) 33, 1553). When 2',3'-dideoxyadenosine (ddA) is synthesized using adenosine as a starting material, nucleic acid bases such as adenine, which result from the cleavage of the glycoside bond of the starting adenosine, and nucleosides such as adenosine (an unreacted starting material), and deoxyadenosine (nucleic acid derivatives) are produced as by-products. When 2',3'-dideoxyinosine (ddI) is synthesized from inosine as a starting material, nucleic acid bases such as hypoxanthine are produced by the cleavage of the glycoside bond of the starting inosine, and nucleosides such as inosine, which is an unreacted starting material, and deoxyinosine (nucleic acid derivatives) are by-produced. DdA or ddI is isolated and purified from a reaction mixture containing such by-products by any one of several methods which include recrystallization, silica gel chromatography and purification on a resin, these methods being known per se. However, because of the physicochemical similarities between the desired compounds and the by-products, such known separation and isolation methods only produce ddA or ddI as the desired compound in extremely low yields when they are to be obtained in high purity, and when complicated procedures are required. Thus, such methods are not industrially applicable purification methods.

In view of the above, when it is desired to isolate ddA from a mixture of ddA and adenine, adenosine, deoxyadenosine or the like, or when it is desired to isolate ddI from a mixture of ddI and hypoxanthine, inosine, deoxyinosine or the like, by resin purification, a modification which has been attempted is the use of a nonpolar porous resin (for example, "SP-207", manufactured by Mitsubishi Kasei Co.) which is often used for the purification of nucleic acid derivatives. Here an aqueous solution of ddA or ddI (pH 7–10) is contacted with the resin, and ddA or ddI is selectively adsorbed. The adsorbed ddA or ddI is eluted with an alcohol. This technique results in the purification of the ddA or ddI (Japanese Patent Applications Laid-Open Hei 1-98496, Hei 1-175990, Hei 1-165390 and Hei-1-175991). However, the purity and the yield of the desired compounds are not always satisfactory. A need therefore continues to exist for an improved method of purifying ddA or ddI.

SUMMARY OF THE INVENTION

Accordingly, one object of the present invention is to provide an industrially advantageous process for isolating and purifying 2',3'-dideoxynucleoside derivatives in high purity and in high yield from mixtures containing impurities.

Briefly, this object and other objects of the present invention as hereinafter will become more readily apparent can be attained in a method for purifying a crude 2',3'-dideoxynucleoside compound by dissolving a crude 2',3'-dideoxynucleoside compound containing nucleic acid impurities in a basic aqueous solution having a pH of not less than 12 and, subsequently, extracting the compound with an organic solvent or crystallizing the same from the basic aqueous solution.

In another embodiment of the present invention, crude 2',3'-dideoxynucleoside is purified by bringing a basic aqueous solution having a pH of not less than 11 containing a crude 2',3'-dideoxynucleoside material into contact with a nonpolar porous resin, whereby the compound is adsorbed on the resin, and then desorbing the thus adsorbed derivative from the resin by treatment with an aqueous solution of an alcohol as the eluent, i.e., the eluting agent.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
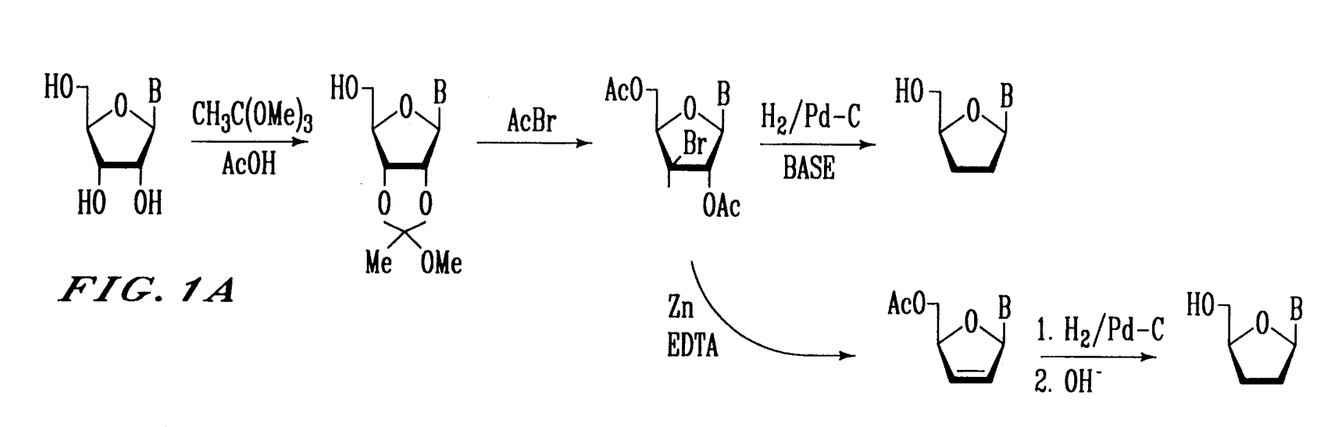
FIG. 1 shows an example of a process for synthesizing ddA and ddI.
Figures 1B, 1C:
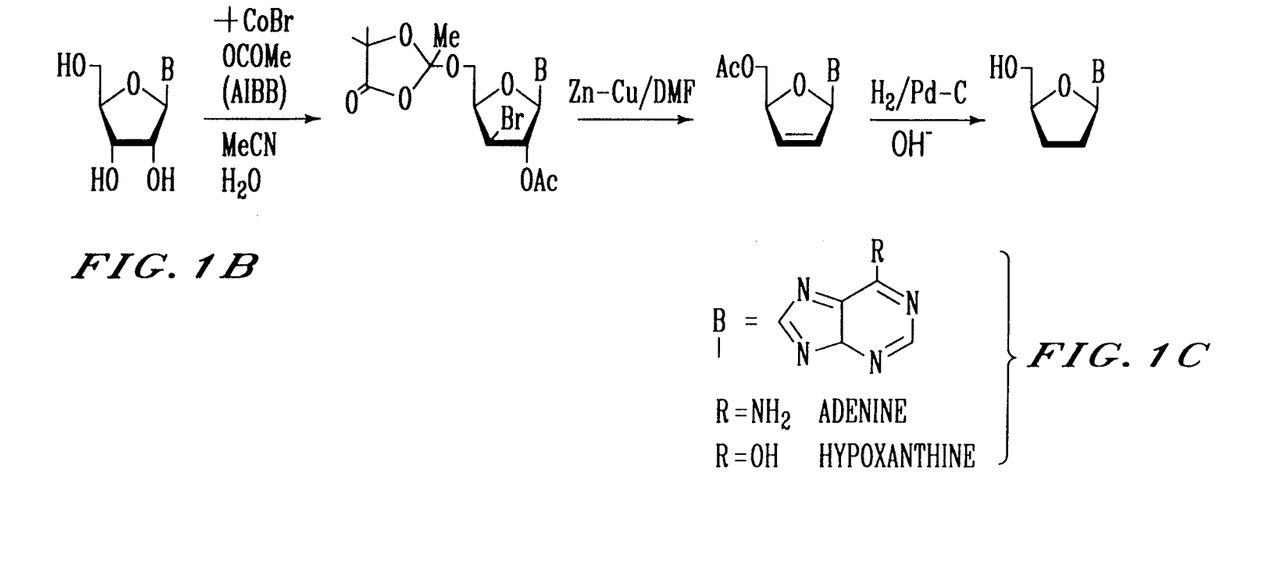

In the first embodiment of the present invention, ddA and ddI can be synthesized, e.g., as is shown in FIG. 1, starting from adenosine and inosine, respectively, by reducing both of the hydroxy groups at the 2' and 3' positions. The final stage of the reaction is a step of removing a protective group for the 5'-hydroxy group of the nucleic acid derivative. Removal of the protective group can be performed as follows. The reaction solution resulting from the reducing reaction, one step prior to the removing step, is rid of the organic solvent by concentration. Water is added to the concentrate and the mixture is made basic by the addition, for example, of an aqueous sodium hydroxide solution. The protective group is thereby removed.

After the deprotection reaction, adenine, adenosine, deoxyadenosine or the like by-products are present in the final reaction solution in addition to the desired ddA. By extraction of the solution, for example, with 2-propanol while keeping the reaction solution basic, the ddA is selectively extracted into the 2-propanol, while the adenine, adenosine and deoxyadenosine remain in the basic aqueous solution, and, as a result, the desired compound and the impurities can be separated with high selectivity. As for ddI, in the final reaction solution after the same deprotection reaction hypoxanthine, inosine, deoxyinosine and the like by-products are present in addition to the desired ddI. By applying alcohol extraction under the same conditions, the ddI is selectively extracted into the alcohol, while the by-products remain in the basic aqueous solution, and, as a result, the desired compound and the impurities can be separated with high selectivity.

Further, when a basic aqueous solution having a pH value of not less than 12 containing ddA, adenine, adenosine, deoxyadenosine, and the like, or a basic aqueous solution having a pH value of not less than 12 containing ddI, hypoxanthine, inosine, a deoxyinosine, and the like, is subjected to crystallization, for example, by concentration and/or cooling, the ddA or ddI can be obtained selectively as crystals in high purity and in high yield. This takes an advantage of the fact that the solubility of the 2',3'-dideoxynucleoside derivatives decreases, whereas the solubilities of the analogous substances do not decrease significantly, whereby the desired compounds can be obtained in high yield. In addition, the desired compounds can be obtained as crystals of a larger crystal size, which, in turn, means that they exhibit improved crystal separation properties. As described above, crystallization under the basic conditions of the present invention can provide an industrially superior purification method.

A product of a higher purity can, of course, be obtained by bringing the desired 2',3'-dideoxynucleoside derivative, once purified by the above-mentioned organic solvent extraction method to a basic aqueous solution, and subjecting the resultant solution to the above-mentioned crystallization methods. Alternatively, the same object can also be attained by applying the two methods in reverse order, i.e., the crystallization method, and then the organic solvent extraction method. As will be described later, other combinations of both methods are also possible.

The 2',3'-dideoxynucleoside derivatives according to the present invention are, for example, 2',3'-dideoxy forms of purine nucleosides such as guanosine, adenosine and inosine and pyrimidine nucleosides such as uridine and cytidine; 2',3'-didehydro forms of such 2',3'-dideoxy forms; and derivatives of such 2',3'-dideoxy forms and such 2',3'-didehydro forms at the sugar portion or base portion thereof. Specific examples include, for example, 2',3'-dideoxynucleosides such as 2',3'-dideoxyadenosine (ddA) and 2',3'-dideoxyinosine (ddI); 2',3'-dideoxy-2',3'-didehydronucleosides; 2',3'-dideoxy-3'-azidonucleosides; 2',3'-dideoxy-2'-fluoronucleosides such as 2',3'-dideoxy-2'-fluoroadenosine and 2',3'-dideoxy-2'-fluoroinosine; and 2',3'-dideoxy-3'-fluoronucleosides Others which can be mentioned are, for example, 2',3'-dideoxy forms of ribonucleosides having a purine base such as 2,6-diaminopurine, 6-chloropurine and 2-aminopurine and pyrimidine nucleosides such as 5'-methyluridine. Thus, it is to be noted that the 2',3'-dideoxynucleoside derivatives of the present invention are defined in a broad sense, including 2',3'-dideoxynucleosides per se, such as ddA and ddI.

The basic conditions employed in this embodiment of the present invention are a pH value of not less than 12, preferably, not less than 13. If the pH is not higher than 11, the separation of impurities is not satisfactory. More specifically, a basic aqueous solution obtained by dissolving a crude 2',3'-dideoxynucleoside in an aqueous solution of an organic or inorganic base of a concentration of 0.1 to 50% by weight, preferably, 1 to 25% by weight can be used.

Suitable bases which can be used to prepare a basic aqueous solution of the present invention include a hydroxide of an alkali metal such as sodium hydroxide or potassium hydroxide or a hydroxide of an alkaline earth metal such as calcium hydroxide. Sodium hydroxide is preferably used.

If the reaction solution has, for example, a pH value of not less than 12 after the completion of the reaction for synthesizing a 2',3'-dideoxynucleoside derivative, such a reaction solution can, of course, be put directly to the purifying treatment of the present invention.

The basic aqueous solution of a crude 2',3'-dideoxynucleoside derivative of the present invention desirably contains 0.1 to 30% by weight, preferably, 1 to 20% by weight of the dideoxynucleoside derivative from the viewpoint of productivity.

Suitable extracting solvents for use in the present invention include organic solvents, for example, alcohols such as 2-propanol, 1-butanol, 2-butanol, 2-methyl-1-propanol, 2-methyl-2-propanol and 1-pentanol; acetonitrile; carboxylic acid esters such as ethyl acetate and methyl acetate; hydrocarbons such as benzene, hexane and toluene; ethers such as diethyl ether, tetrahydrofuran and dioxane; halogenated hydrocarbons such as dichloromethane, chloroform and dichloroethane, and ketones such as methyl ethyl ketone. Alcohols are, however, preferred from the view point of extraction ratio. Such a solvent is usually used in an amount of 0.1 to 10 times the volume of the basic aqueous solution of the crude 2',3'-dideoxynucleoside derivative.

There is no particular restriction on the extraction temperature, and extraction can be conducted at 0° to 100° C.

Extraction under such conditions can be shortened in time by shaking or stirring. The extraction is usually completed in about 1 min to 24 hours.

After completion of the extraction, the organic solvent layer containing the desired compound is separated, and concentrated by a method known per se, e.g., removing the solvent by distillation, whereby the desired 2',3'-dideoxynucleoside derivative is crystallized and can be easily isolated from the remainder. The desired compound can be recovered with a higher efficiency by adding water in the course of removing the extraction solvent and forming a concentrated aqueous solution by concentration. In this case, the desired compound of a high purity can be isolated by crystallizing it from a basic aqueous solution in accordance with the present invention.

The crystallization of the present invention can be conducted by a known method such as, for example, by concentrating a basic aqueous solution of a 2',3'-dideoxynucleoside derivative preferably under reduced pressure, more preferably, at 1–200 mmHg and, optionally, with heating to 30°–100° C., followed by cooling. The concentration for crystallization varies depending on the desired compound, and normally ranges from 5 to 100 g/dl.

When the resultant concentrated solution is allowed to cool to room temperature or, if required, cooled to about 0° C., crystals of the 2',3'-dideoxynucleoside derivative are precipitated and easily separated by an operation such as filtration.

In the second embodiment of the present invention, ddA and ddI can be synthesized, e.g., as is shown in FIG. 1, starting from adenosine and inosine, respectively, by reducing both hydroxy groups at the 2' and 3'positions.

Crude crystals of ddA and ddI obtained by the above-mentioned reaction contain, in addition to each of the desired ddA and ddI, impurities such as adenosine (starting material), adenine (a nucleic acid base resulting from the cleavage of the glycoside bond of the starting adenosine), deoxyadenosine, and the like by-products in the case of the synthesis of ddA, and impurities, for example, inosine, hypoxanthine and deoxyinosine in the same manner in the case of ddI, respectively. The present inventors have succeeded in separating ddA and ddI from their impurities, respectively, by dissolving the crude crystals in a basic aqueous solution having a pH value of not less than 11 using, for example, an aqueous solution of sodium hydroxide, and then bringing the basic aqueous solution into contact with a nonpolar porous resin, e.g., by feeding the same, for example, into a resin column. It has been found that a significant difference in adsorptivity on the resin exists between ddA and such impurities as adenine, adenosine, and, in particular, deoxyadenosines. Similarly, there is a significant difference in adsorptivity between ddI and hypoxanthine, inosine, and, in particular, deoxyinosines.

The process embodiment is usually practiced as follows: A basic aqueous solution of a crude 2',3'-dideoxynucleoside derivative is fed into a column packed with a nonpolar porous resin whereby the 2',3'-dideoxynucleoside derivative is adsorbed on the resin, and then neutrality is restored in the column by washing the column with water (known per se as a conventional adsorbing procedure), and successively an aqueous solution of an alcohol is passed through the column, which elutes only the desired 2',3'-dideoxynucleoside derivative.

The basic conditions in this embodiment of the present invention are a pH value of not less than 11, preferably, not less than 12. If the pH is not higher than 11, separation from impurities is not sufficient. Specifically, a basic aqueous solution obtained by dissolving a crude 2',3'-dideoxynucleoside derivative in an aqueous solution of an inorganic base having a concentration of 0.1–30 wt % can be used.

According to the present invention the bases to be used for preparing a basic aqueous solution of a crude 2',3'-dideoxynucleoside derivative include inorganic bases such as sodium hydroxide and potassium hydroxide, and for example, ammonia. Among those bases, sodium hydroxide is used preferably. Further, when using sodium hydroxide, for example, sodium chloride may be added in an amount about equal to that of sodium hydroxide. the salt further improves the separation, probably because of the ionic effect.

If a reaction solution has, for example, a pH value of not less than 11 after the synthesis reaction of a 2',3'-dideoxynucleoside derivative, such a reaction solution can, of course, be subjected directly to the method of the present invention.

The 2',3'-dideoxynucleoside derivatives of the present invention are just the same as those mentioned hereinabove in connection with the first embodiment.

As the nonpolar porous resin to be used in the present invention, any polymer of the styrene—divinylbenzene system, or derivatives of such polymers can be used. For instance, a member of "Dianion" series, and "SP" series (both manufactured by Mitsubishi Kasei Co.), a "XAD-4" (manufactured by Rohm & Haas Co.) and "OC-1031" (manufactured by Bayer Co.) can be used. In addition, other nonpolar porous resins may be used so long as they have equivalent performance. In particular, "SP-207" increased in specific gravity (manufactured by Mitsubishi Kasei Co.) is excellent in handling, since the resin does not float.

A nonpolar porous resin and a basic aqueous solution of a crude 2',3'-dideoxynucleoside derivative are brought into contact with each other either by passing the basic aqueous solution, as described above, through a resin column (column method) or by adding a nonpolar porous resin to a basic aqueous solution of a crude 2',3'-dideoxynucleoside derivative, whereby the desired 2',3'-dideoxynucleoside derivative is adsorbed on the resin. Subsequently, the resin is removed (batchwise method). The column method is convenient and preferred in view of the operation.

In the case of the column method, there is no particular restriction on the rate of fluid flow through the column, and it is suitably SV=0.5–10, preferably, SV=about 1–4.

In the case of the column method, the volume amount of the basic aqueous solution of a crude 2',3'-dideoxynucleoside derivative loaded on the column varies depending on the kind of 2',3'-dideoxynucleoside derivative and the concentration of the solution. The amount of 2',3'-dideoxynucleoside derivative loaded generally ranges from 1 to 2,000 g, preferably, 40 to 500 g based on 1,000 ml of the resin, from the view point of separability and economy.

In the batchwise method, a nonpolar porous resin is used in an amount of 0.1 to 100 ml, preferably, 0.5 to 5 ml per 1 g of a crude 2',3'-dideoxynucleoside derivative There is no particular restriction on the temperature of contact between a nonpolar porous resin and the basic aqueous solution of a crude 2',3'-dideoxynucleoside derivative, and it is usually within a range from 10° to 50° C. The purifying performance of the resin remains substantially unchanged within the range.

The amount of water used for eluting, that is, desorbing the 2',3'-dideoxynucleoside derivative adsorbed on the nonpolar porous resin therefrom is properly selected from within the range from 1 to 20 RV.

As for the alcohols used to prepare an aqueous alcohol solution for elution, a lower alcohol such as methanol, ethanol or 2-propanol is preferred. A preferred concentration of the alcohol, as an appropriate eluting condition, is from 10 to 50 vol %. The amount to be used is properly selected from within a range from 1 to 20 RV.

There is also no particular restriction on the method of recovery of 2',3'-dideoxynucleoside derivative as the desired substance from the eluate. For instance, after the completion of the elution, eluted fractions of the 2',3'-dideoxynucleoside derivative are collected. The alcohol is then removed by distillation by concentration under reduced pressure, the residue is concentrated to crystallize the desired compound, and finally the deposited crystals are isolated.

Having generally described this invention, a further understanding can be obtained by reference to certain specific examples which are provided herein for purposes of illustration only and are not intended to be limiting unless otherwise specified.

Example 1

(Synthesis Example)

Synthesis (a): Synthesis of 2',3'-dideoxyadenosine (ddA) from adenosine (1)

To a solution of 20 g (74.9 mmol) of adenosine in 100 ml of acetic acid, 11.7 ml (1.3 equivalent amount) of trimethyl orthoacetate was added and stirred at 50° C. for 3 hours. After concentrating the reaction solution under reduced pressure, 100 ml of acetonitrile was added. The resulting mixture was cooled to 10° C., and 22 ml of acetyl bromide (4 equivalent amount) was added dropwise thereto over a period of 1 hour. After stirring the reaction solution for a further 2 hours at 15° C., it was neutralized with an aqueous solution of sodium carbonate and then subjected to extraction with acetonitrile. 3 g (5 mol %) of 10% palladium on carbon (10% Pd—C catalyst) was added to the liquid extract, and then hydrogenation was carried out under a hydrogen atmosphere at room temperature for 5 hours, while controlling the pH value of the system to 9.5 with an aqueous solution of sodium hydroxide (NaOH). The reaction solution was filtered after the completion of the reaction. The solvent was removed by distillation from the filtrate under reduced pressure, and an aqueous NaOH solution was added to the residue. The mixture was stirred for 5 hours while keeping the pH value of the mixture at 12.

The 1000 ml aqueous alkaline solution (pH 12) thus obtained contained various nucleic acid derivatives in the composition shown in Table 1.

TABLE 1

| Composition A | | |
|---|---|---|
| 2',3'-dideoxyadenosine (ddA) | 12.23 g | 52.0 mmol |
| 3'-deoxyadenosine (3dA) | 2.52 | 10.0 |
| Adenosine (AR) | 0.89 | 3.3 |
| Adenine (Ad) | 0.69 | 5.1 |

Synthesis (b): Synthesis of 2',3'-dideoxyadenosine (ddA) from adenosine (2)

To a solution of 20 g (74.9 mmol) of adenosine in 100 ml of acetic acid, 11.7 ml (1.3 equivalent amount) of trimethyl orthoacetate was added, and the mixture was stirred at 50° C. for 3 hours. After concentrating the reaction solution under reduced pressure, 100 ml of acetonitrile was added. The resulting mixture was cooled to 10° C., and 22 ml of acetyl bromide (4 equivalent amount) was added dropwise thereto over a period of 1 hour. The reaction solution was stirred for a further 2 hours at 15° C., neutralized with an aqueous solution of sodium carbonate, and then subjected to extraction with acetonitrile. 7.8 g (2 equivalent amount) of zinc (Zn) powder was added to the liquid extract, and the mixture was stirred at room temperature for 2 hours. The reaction solution was poured into a solution of 90 g (4 equivalent amount) of disodium ethylenediamine tetraacetate dihydrate (EDTA·2Na·2H$_2$O) adjusted to pH 7 with an aqueous NaOH solution, and then subjected to extraction with 200 ml of acetonitrile. 3 g (5 mol %) of a 10% Pd—C catalyst was added to the liquid extract, and then hydrogenation was carried out under a hydrogen atmosphere at room temperature for 5 hours. The reaction solution was filtered after the reaction was over. The solvent was removed by distillation from the filtrate under reduced pressure. An aqueous NaOH solution was added to the residue, and the mixture was stirred for 5 hours while keeping the pH value of the mixture at 12.

The 1000 ml aqueous alkaline solution (pH 12) thus obtained contained various nucleic acid derivatives in the amounts shown in Table 2.

TABLE 2

| Composition B | | |
|---|---|---|
| ddA | 11.78 g | 50.1 mmol |
| AR | 0.86 | 3.2 |
| Ad | 1.84 | 13.6 |

Synthesis (c): Synthesis of 2',3'-dideoxyadenosine (ddA) from adenosine (3)

To a slurry solution of 20 g (74.9 mmol) of adenosine in 200 ml of acetonitrile, 0.67 ml (37.5 mmol) of water and 47.0 g (224.7 mmol, 3 equivalent amount) of acetoxyisobutyryl bromide were added. Reaction was carried out at room temperature for 2 hours. The reaction mixture was neutralized with an aqueous 10% solution of sodium hydrogen carbonate, and the aqueous layer was removed using a separatory funnel. 19.3 g (2 equivalent amount) of zinc-copper complex (Zn—Cu complex) was added to the organic layer, and the mixture was stirred at room temperature for 2 hours. The reaction solution was poured into a solution of 90 g (4 equivalent amount) of EDTA·2Na·2H$_2$O adjusted to pH 7 with an aqueous NaOH solution, and subjected to extraction with 200 ml of acetonitrile. 3 g (5 mol %) of a 10% Pd—C catalyst was added to the liquid extract and then hydrogenation was carried out under a hydrogen atmosphere at room temperature for 5 hours. The reaction solution was filtered after the reaction was over. The solvent was removed by distillation from the filtrate under reduced pressure. An aqueous NaOH solution was added to the residue, and the mixture was stirred for 5 hours while keeping the pH value of the mixture at 12.

The 1000 ml aqueous solution (pH 12) thus obtained contained various nucleic acid derivatives in the amounts shown in Table 3.

TABLE 3

| Composition C | | |
|---|---|---|
| ddA | 9.12 g | 38.8 mmol |
| AR | 4.35 | 16.3 |
| Ad | 1.63 | 12.1 |

EXAMPLE 2

The saponified solution of Composition A obtained in Example 1, Synthesis (a) was adjusted to pH 7 with hydrochloric acid. Four 10-ml portions were taken from the pH-adjusted solution, and four kinds of test solutions were prepared using a first of the four portions as it was and by adding NaOH in such amounts as to provide 1, 10 and 20 wt % concentrations, respectively, to a second, a third and a fourth solution. The pH values of the four test solutions were 7, >13, >13 and >13. 10 ml of 2-methyl-1-propanol was added to each of the test solutions, and mixed sufficiently. Each mixture was then allowed to stand for phase separation.

The concentration of each nucleic acid derivative in the organic layer and the aqueous layer of each of the formulations was analyzed by high performance liquid chromatography (HPLC), to determine distribution coefficients (organic layer/aqueous layer) and ddA purities in the organic layer. The results are shown in Table 4.

TABLE 4

| NaOH (%) | Nucleic acid derivative | Distribution *1) coefficient | Purity *2) (%) |
|---|---|---|---|
| 0 (Comparative) (pH = 7) | ddA | 1.32 | 77.7 |
| | 3dA | 0.96 | |
| | AR | 0.49 | |
| | Ad | 1.62 | |
| 1 (Inventive) (pH > 13) | ddA | 1.37 | 90.6 |
| | 3dA | 0.27 | |
| | AR | 0.07 | |
| | Ad | 0.16 | |
| 10 (Inventive) (pH > 13) | ddA | 4.15 | 94.6 |
| | 3dA | 0.11 | |
| | AR | 0.04 | |
| | Ad | 0.24 | |
| 20 (Inventive) (pH > 13) | ddA | 8.67 | 96.0 |
| | 3dA | 0.1 | |
| | AR | 0.02 | |
| | Ad | 0.31 | |

*1: g/dl (organic layer)/g/dl (aqueous layer)
*2: ddA purity in the organic layer As apparent from the above table, the distribution coefficient of ddA increases and the distribution coefficients of the impurities: 3'-deoxyadenosine (3 dA), adenosine (AR) and adenine (Ad) decrease as the NaOH concentration increases. As a result, ddA was extracted into the organic layer in high purity and high yield.

The saponified solutions of Compositions B and C obtained in Example 1, Syntheses (b) and (c) were treated quite in the same manner as the saponified solution of Composition A obtained in Example 1, Synthesis (a), to obtain the results shown in Tables 5 and 6, respectively.

TABLE 5

| NaOH (%) | Nucleic acid derivative | Distribution coefficient | Purity (%) |
|---|---|---|---|
| 0 (Comparative) | ddA | 1.53 | 79.0 |
| | AR | 0.52 | |
| | Ad | 1.91 | |
| 1 (Inventive) | ddA | 1.55 | 96.5 |
| | AR | 0.11 | |
| | Ad | 0.23 | |
| 10 (Inventive) | ddA | 6.03 | 97.2 |
| | AR | 0.03 | |
| | Ad | 0.13 | |
| 20 (Inventive) | ddA | 9.25 | 97.7 |
| | AR | 0.00 | |
| | Ad | 0.15 | |

TABLE 6

| NaOH (%) | Nucleic acid derivative | Distribution coefficient | Purity (%) |
|---|---|---|---|
| 0 (Comparative) | ddA | 1.39 | 69.3 |
| | AR | 0.64 | |
| | Ad | 2.34 | |
| 1 (Inventive) | ddA | 1.52 | 93.6 |
| | AR | 0.06 | |
| | Ad | 0.16 | |
| 10 (Inventive) | ddA | 5.94 | 95.6 |
| | AR | 0.01 | |
| | Ad | 0.24 | |
| 20 (Inventive) | ddA | 7.86 | 97.5 |
| | AR | 0.00 | |
| | Ad | 0.07 | |

As seen from both tables, the distribution coefficient of ddA for the saponified solutions obtained in Example 1, Syntheses (b) and (c), also increases, while the distribution coefficients of the impurities: AR and Ad decrease, as the NaOH concentration increases. Similar to Example 1, Synthesis (a), ddA was extracted into the organic layer in high purity and high yield.

EXAMPLE 3

A mixture consisting of 1.0 g of ddA, 100 mg of 3 dA, 100 mg of AR and 100 mg of Ad was added to 100 ml of water (solvent 1) and dissolved by heating to 60° C. The solution was concentrated under reduced pressure (10 mmHg) at room temperature until crystals were formed and then cooled to 5° C.

The crystals were collected by filtration and dried. The dried crystals were analyzed by HPLC, whereby the purity of the crystals and the recovery yields of each nucleic acid derivative were measured.

The same experiment was repeated also for the other solvents (2)–(6) indicated in Table 7 below. The temperature for dissolution by heating was, however, 50° C. in the case of solvents (5) and (6).

TABLE 7

| Solvent | Nucleic acid derivative | Crystal *1) purity (%) | Recovery yield (%) |
|---|---|---|---|
| (1) H$_2$O (Comparative) | ddA | 95.3 | 51.2 |
| | 3dA | | 1.05 |
| | AR | | 0.81 |
| | Ad | | 1.86 |
| (2) 1% NaOH (Inventive) | ddA | 98.7 | 67.5 |
| | 3dh | | 0.3 |
| | AR | | 0.4 |
| | Ad | | 0.3 |
| (3) 10% NaOH (Inventive) | ddA | 99.4 | 86.1 |
| | 3dA | | 0.2 |
| | AR | | 0.4 |
| | Ad | | 0.0 |
| (4) 20% NaOH (Inventive) | ddA | 100.0 | 93.4 |
| | 3dA | | 0.0 |
| | AR | | 0.0 |
| | Ad | | 0.0 |
| (5) MeOH (Comparative) | ddA | 75.9 | 83.1 |
| | 3dA | | 96.4 |
| | AR | | 92.5 |
| | Ad | | 15.4 |
| (6) CHCl$_3$/MeOH (Comparative) | ddA | 74.6 | 91.4 |
| | 3dA | | 98.8 |
| | AR | | 97.6 |
| | Ad | | 26.4 |

1*): g/g-crystal

It can be seen from the above table that, when solutions have a higher NaOH concentration, ddA crystals can be obtained by recrystallization in a higher yield and have a higher purity, containing no or little amounts of 3 dA, AR and Ad.

EXAMPLE 4

To one liter of a saponified solution (containing 115.05 g of ddA, 13.10 g of 3 dA, 2.04 g of 2 dA, 4.07 g of AR and 3.67 g of Ad) obtained by the same reaction procedures as set forth in Example 1, Synthesis (a), 1 liter of an aqueous 25% NaOH solution was added. The mixture was then subjected to extraction three times, each time with 1 liter of 2-propanol.

The extracted propanol layer was concentrated, while adding 250 ml of water. In the course of the process, 200 ml of an aqueous 25% NaOH solution was added and stirred. The mixture was then subjected to crystallization by cooling to 20° C. Pure ddA crystals were collected by filtration.

ddA crystals having a high purity were obtained by the combination of the extraction operation and the crystallizing operation under the basic condition described above. The contents and the compositions of the nucleic acid derivatives at each of the stages: saponified solution, 2-propanol extract and crystals after recrystallization were measured by HPLC. The results are shown in Table 8.

TABLE 8

| Stage | Contents of nucleic acid derivatives (g) | | | | |
|---|---|---|---|---|---|
| | ddA (purity (%)) | 3dA | 2dA | AR | Ad |
| Saponified solution | 115.05 (82.7) | 13.1 | 2.04 | 4.07 | 3.67 |
| Isopropanol extract | 107.43 (97.3) | 1.03 | 0.00 | 0.00 | 1.19 |
| Recrystallized crystals | 102.55 (99.9) | 0.07 | 0.00 | 0.00 | 0.00 |

EXAMPLE 5

(Synthesis Example)
Synthesis (a): Synthesis of 2',3'-dideoxyadenosine (ddA) from adenosine (4)

To a solution of 20 g (74.9 mmol) of adenosine in 100 ml of acetic acid, 11.7 ml (1.3 equivalent amount) of trimethyl orthoacetate was added. The mixture was stirred at 50° C. for 3 hours. After the reaction solution had been concentrated under reduced pressure, 100 ml of acetonitrile was added. The resulting mixture was cooled to 10° C., and 22 ml (4 equivalent amount) of acetyl bromide was dropwise over a period of 1 hour. After stirring the reaction solution for a further 2 hours at 15° C., it was neutralized with an aqueous solution of sodium carbonate ($Na_2CO_3$) and was then subjected to extraction with acetonitrile. 3 g (5 mol %) of a 10% palladium on carbon (10% Pd—C catalyst) was added to the liquid extract, and then hydrogenation was carried out under a hydrogen atmosphere at room temperature for 5 hours, while the pH of the system was controlled to 9.5 with an aqueous solution of sodium hydroxide (NaOH). The reaction solution was filtered after the reaction was over. The solvent was removed by distillation from the filtrate under reduced pressure, and an aqueous NaOH solution was added to the residue. The mixture was stirred for 5 hours while keeping the pH value of the mixture at 12.

The 100 ml aqueous alkaline solution thus obtained contained the various nucleic acid derivatives in the composition shown in Table 9.

TABLE 9

| Composition D | | |
|---|---|---|
| 2',3'-dideoxyadenosine (ddA) | 12.18 g | 51.8 mmol |
| 3'-deoxyadenosine (3dA) | 2.45 | 9.8 |
| 2'-deoxyadenosine (2dA) | 0.37 | 1.5 |
| Adenosine (AR) | 0.86 | 3.2 |
| Adenine (Ad) | 0.61 | 4.5 |

Synthesis (b): Synthesis of 2',3'-dideoxyinosine (ddI) from inosine (1)

To a solution of 20 g (74.6 mmol) of inosine in 100 ml of acetic acid, 11.7 ml (1.3 equivalent amount) of trimethyl orthoacetate was added, and the mixture was stirred at 50° C. for 3 hours. After the reaction solution had been concentrated under reduced pressure, 200 ml of acetonitrile was added. The resulting mixture was cooled to 5° C., and 22 ml (4 equivalent amount) of acetyl bromide was added dropwise over a period of 2 hours. The reaction solution was stirred for a further 3 hours at 5° C., neutralized with an aqueous solution of sodium carbonate, and then subjected to extraction with acetonitrile. 3 g (5 mol %) of a 10% Pd—C catalyst and 30 ml (5 equivalent amount) of triethylamine was added to the liquid extract. The mixture was subjected to hydrogenation under a hydrogen atmosphere at room temperature for 5 hours. After the completion of the reaction, the reaction solution was filtered, and the solvent was removed by distillation under reduced pressure. An aqueous NaOH solution was added to the residue. The mixture was stirred for 5 hours while keeping the pH value of the mixture at 12.

The 1000 ml aqueous alkaline solution thus obtained contained, various nucleic acid derivatives in the composition shown in Table 10.

TABLE 10

| Composition E | | |
|---|---|---|
| 2',3'-dideoxyinosine (ddI) | 9.53 g | 40.4 mmol |
| 3'-deoxyinosine (3dI) | 4.56 | 18.1 |
| Inosine (HxR) | 2.35 | 8.8 |
| Hypoxanthine (Hx) | 0.68 | 5.0 |

Synthesis (c): Synthesis of 2',3'-dideoxyinosine (ddI) from inosine (2)

To a solution of 20 g (74.6 mmol) of inosine in 100 ml of acetic acid, 11.7 ml (1.3 equivalent amount) of trimethyl orthoacetate was added, and the mixture was stirred at 50° C. for 3 hours. After concentrating the reaction solution under reduced pressure, 200 ml of acetonitrile was added. The resulting mixture was cooled to 5° C., and 22 ml (4 equivalent amount) of acetyl bromide was added dropwise over a period of 2 hours. The reaction solution was stirred for a further 3 hours at 5° C., neutralized with an aqueous solution of sodium carbonate, and then subjected to extraction with acetonitrile. 7.8 g (2 equivalent amount) of a zinc (Zn) powder was added to the liquid extract, and the mixture was stirred for 2 hours at room temperature. The reaction solution was poured into a solution of 90 g (4 equivalent amount) of disodium ethylenediamine tetraacetate dihydrate ($EDTA \cdot 2Na \cdot 2H_2O$) adjusted to pH 7 with an aqueous NaOH solution, and subjected to extraction with 200 ml of acetonitrile. 3 g (5 mol %) of a 10% Pd—C catalyst was added to the liquid extract, and the mixture was then subjected to hydrogenation under a hydrogen atmosphere at room temperature for 5 hours. The reaction solution was filtered after the reaction was over, and the solvent was removed by distillation from the filtrate under reduced pressure. An aqueous solution of sodium hydroxide was added to the residue, and the mixture was stirred for 5 hours while keeping the pH value of the mixture at 12.

The 1000 ml aqueous alkaline solution thus obtained contained, various nucleic acid derivatives in the amounts shown in Table 11.

TABLE 11

| Composition F | | |
|---|---|---|
| ddI | 9.13 g | 38.7 mmol |
| HxR | 2.56 | 9.6 |
| Hx | 1.38 | 10.1 |

Synthesis (d): Synthesis of 2',3'-dideoxyinosine (ddI) from inosine (3)

To a slurry solution of 20 g (74.6 mmol) of inosine in 200 ml of acetonitrile, 0.67 ml (37.5 mmol) of water and 47.0 g (224.7 mmol, 3 equivalent amount) of acetoxyisobutyryl bromide were added. A reaction was carried out at room temperature for 2 hours. The resulting reaction mixture was neutralized with an aqueous 10% solution of sodium hydrogen carbonate ($NaHCO_3$), and the aqueous layer was removed by phase separation. 19.3 g (2 equivalent amount) of zinc-copper complex (Zn—Cu complex) was added to the organic layer, and the mixture was stirred at room temperature for 2 hours. The reaction mixture was poured into a solution of 90 g (4 equivalent amount) of EDTA·2Na·2H$_2$O adjusted to pH 7 with an aqueous NaOH solution, and subjected to extraction with 200 ml of acetonitrile. 3 g (5 mol %) of a 10% Pd—C catalyst was added to the liquid extract, and then hydrogenation was carried out under a hydrogen atmosphere at room temperature for 5 hours. The reaction solution was filtered after the reaction was over, and the solvent was removed by distillation from the filtrate under reduced pressure. An aqueous solution of sodium hydroxide was added to the residue, and the mixture was stirred for 5 hours while keeping the pH value of the mixture at 12.

The thus obtained aqueous alkaline solution of ddI contained, per 1000 ml, various nucleic acid derivatives in the amounts shown in Table 12.

TABLE 12

| Composition G | | |
|---|---|---|
| ddI | 4.31 g | 18.3 mmol |
| HxR | 2.92 | 10.9 |
| Hx | 1.57 | 11.5 |

Comparative Example 1

The saponified solution of Composition D obtained in Example 5, Synthesis (a), was adjusted to pH 10 with 4N hydrochloric acid, and fed to a column (30 mm$\phi$×600 mm) packed with a nonpolar porous resin "SP-207" (ddA 30 g/l—resin concentration). Then, the ddA was eluted while changing the eluent as follows: water→15% MeOH→30% MeOH.

Figure 2:
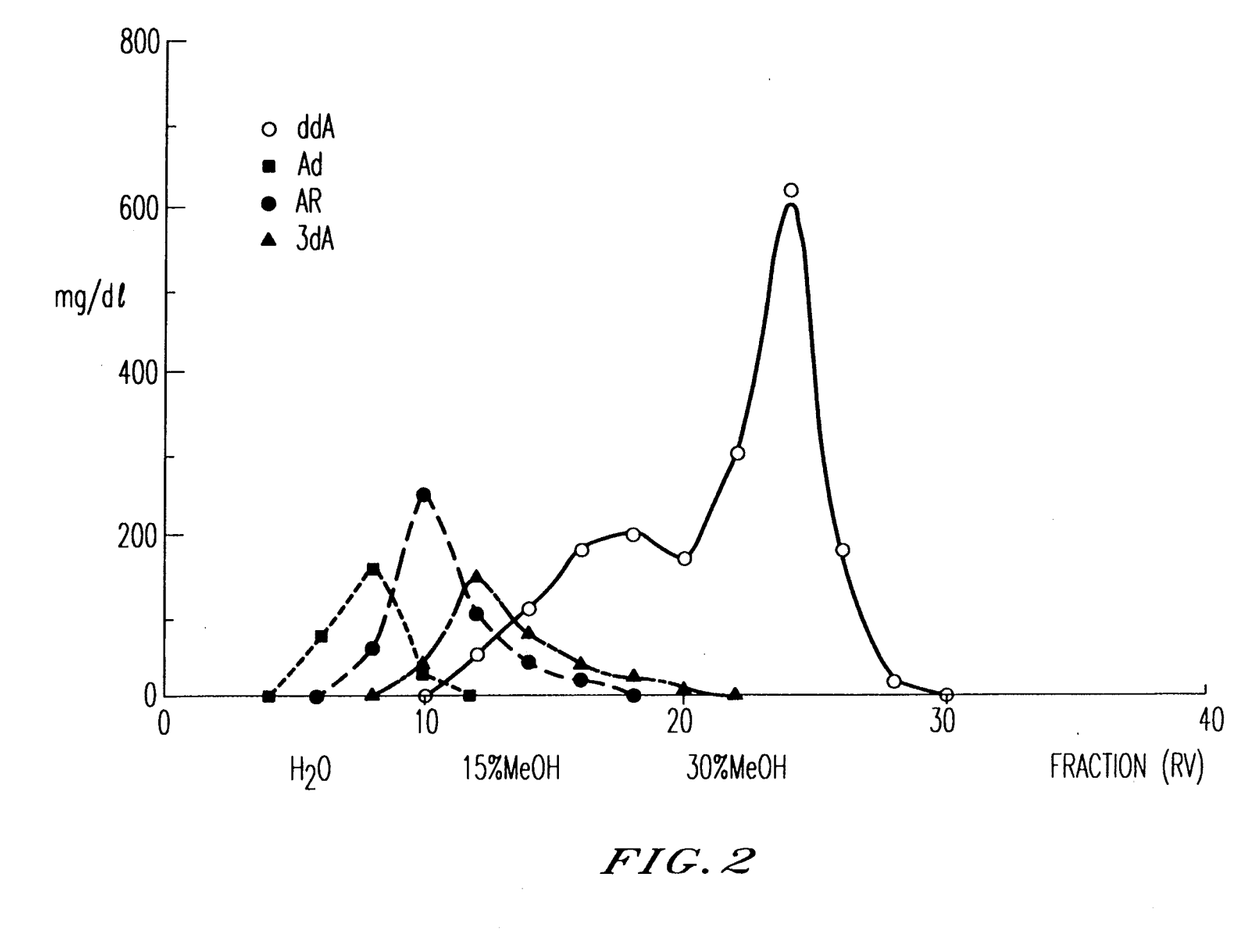
FIG. 2 shows an elution curve in Comparative Example 1.

The ddA eluted fractions overlapped with those of the impurities: Ad, AR and 3 dA (Refer to FIG. 2), and the purity was as low as 80% if a 90% fraction was to be recovered, whereas only about a 50% fraction could be recovered at a purity higher than 99%. Further, the eluent was required in as much an amount as 30 RV in terms of the sum of the water and the aqueous methanol solution.

Comparative Example 2

The saponified solution of Composition G obtained in Example 5, synthesis (d), was adjusted to pH 8 with 4N hydrochloric acid, and fed to a column packed with the "SP-207" resin (30 g/l—resin concentration). Then, the ddI was eluted while changing the eluent as follows: water→10% MeOH→30% MeOH.

Figure 3:
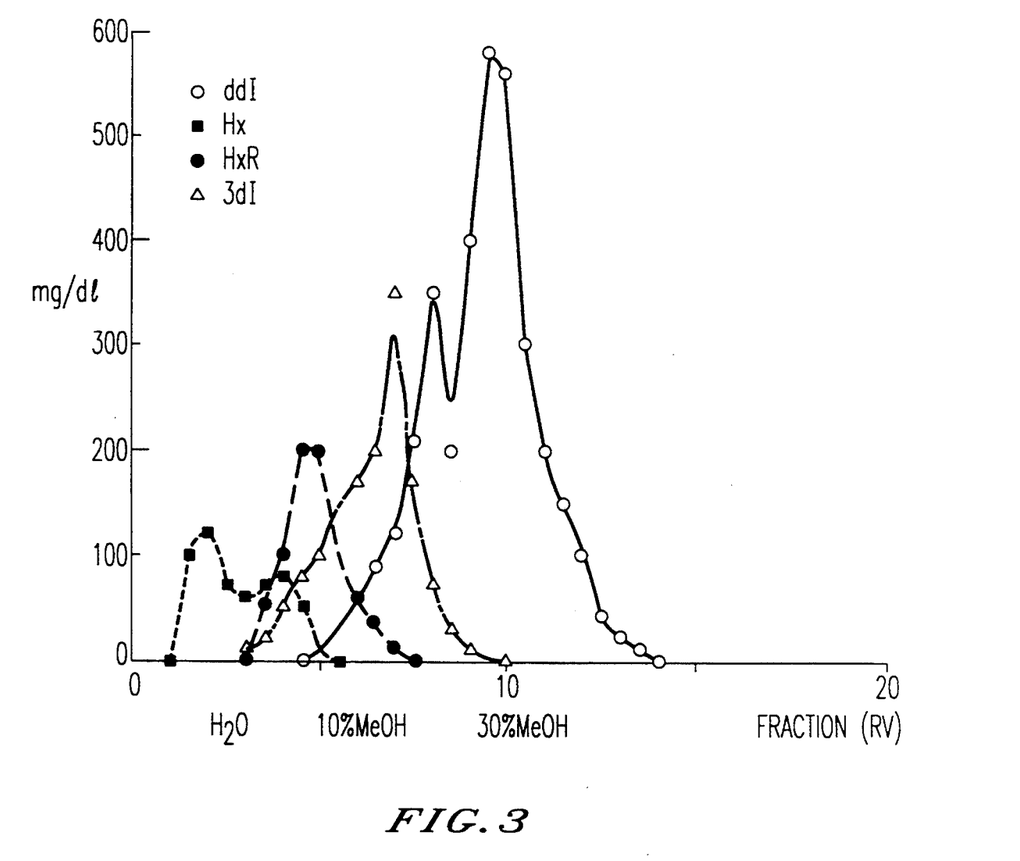
FIG. 3 shows an elution curve in Comparative Example 2.

The ddI eluted fractions overlapped with those of the impurities: Hx, HxR and 3dI (Refer to FIG. 3) and the purity was as low as 75% if a 90% fraction was to be recovered, whereas only about a 35% fraction could be recovered at a purity higher than 99%. Further, the eluent was required in an amount of as much as 15 RV.

EXAMPLE 6

Figure 4:
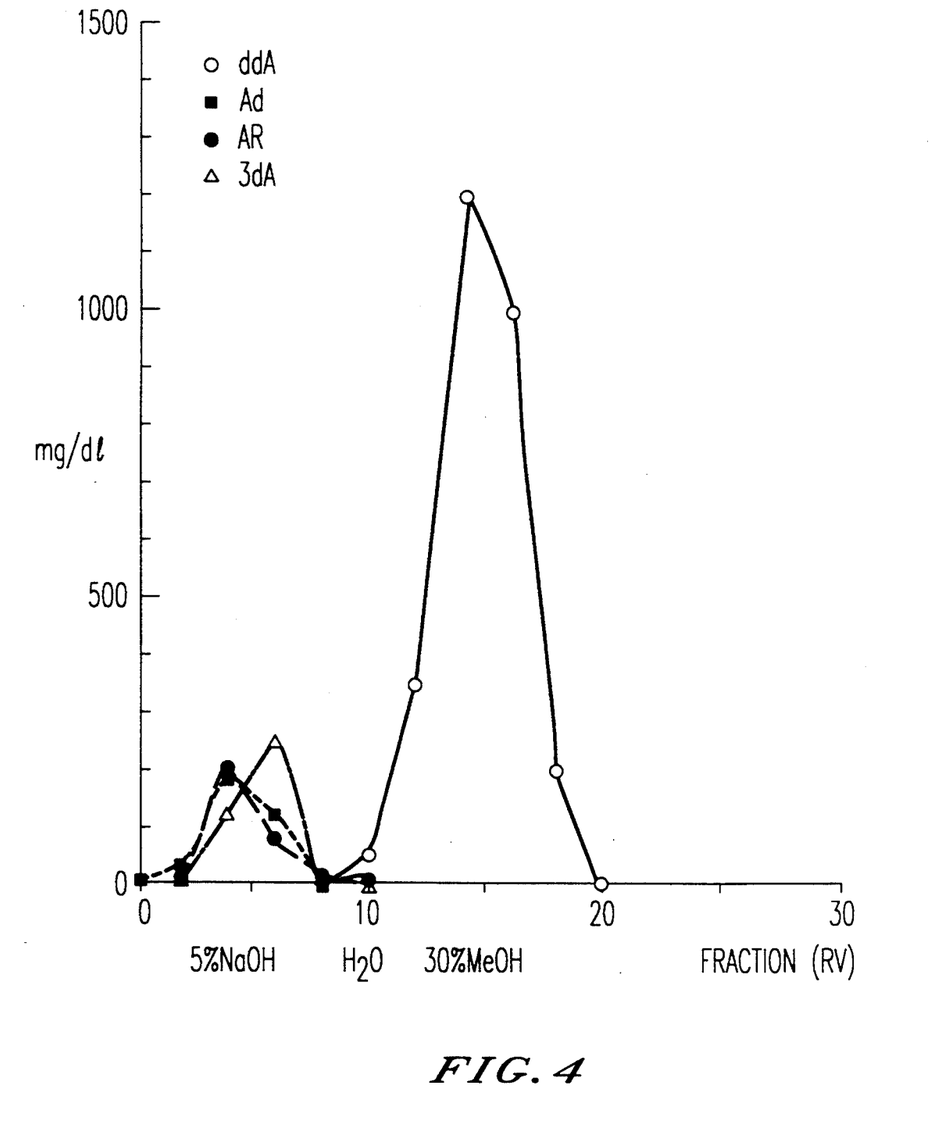
FIG. 4 shows an elution curve in Example 6.

NaOH was added to the saponified solution of Composition D obtained in Example 5, Synthesis (a), so as to give 5% concentration, and the mixture was fed to a column packed with the "SP-207" resin in twice the amount of the resin in Comparative Example 1 for adsorption on the resin (60 g/l—resin concentration). The impurities Ad, AR and 3 dA were rapidly eluted, while the ddA wasn't. After the elution of the impurities, the eluent was replaced with water (1 RV) and further with 30% MeOH (Refer to FIG. 4).

As a result, a ddA elution fraction having high purity could be recovered in a high yield (Refer to Table 13) and with a total liquid amount of 20 RV.

ddA crystals of a purity higher than 99% were obtained by concentration/crystallization from the elution fraction in a yield of 90%.

EXAMPLE 7

Figure 5:
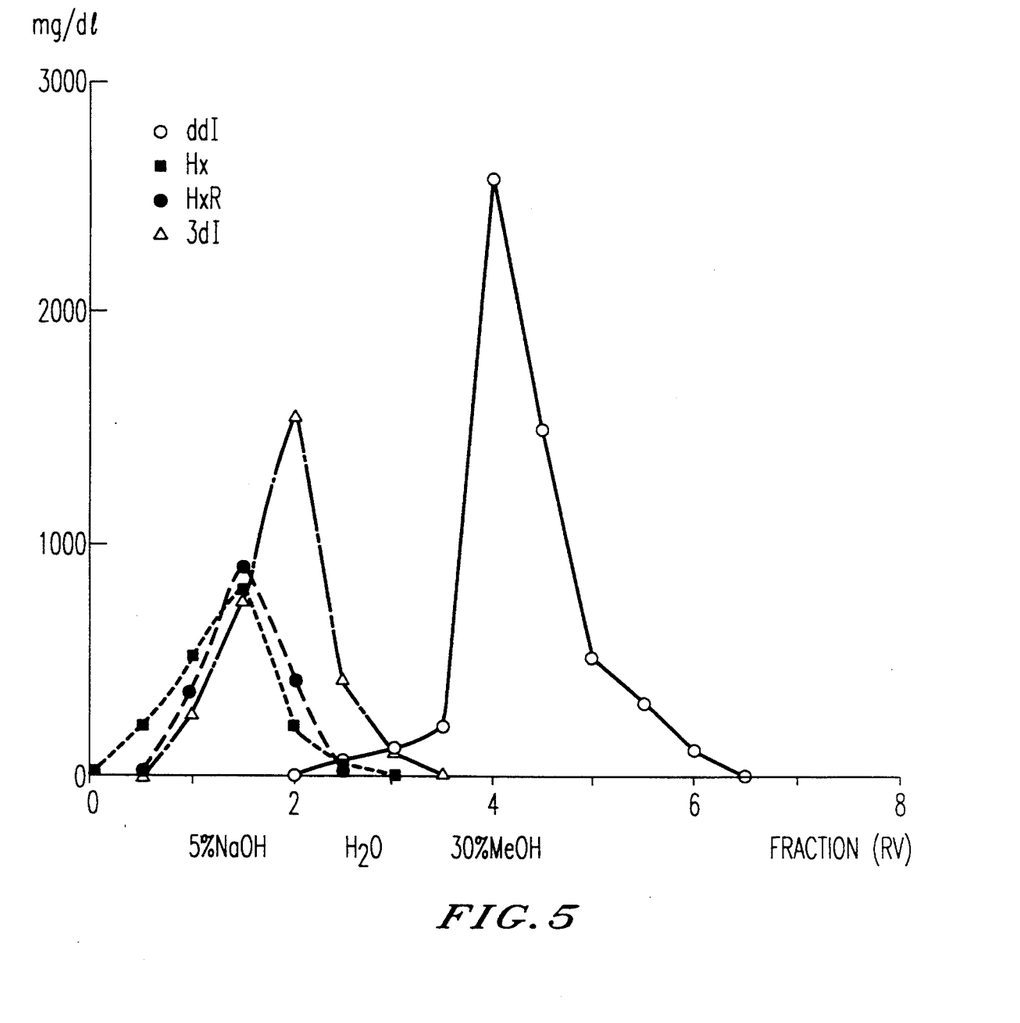
FIG. 5 shows an elution curve in Example 7.

NaOH was added to the solution of Composition G obtained in Example 5, Synthesis (d), to form an aqueous solution having a 5% concentration of NaOH. When the mixture was fed to a column packed with the "SP-207" resin for adsorption (30 g/l—resin concentration), the impurities Hx, HxR and 3dI were eluted rapidly, while the ddI wasn't. After the elution of the impurities, the eluent was replaced with water (1 RV) and further with 30% MeOH (Refer to FIG. 5).

As a result, a ddI elution fraction of high purity could be recovered in high yield (Refer to Table 13) and with a total liquid amount of 7 RV.

EXAMPLE 8

Figure 6:
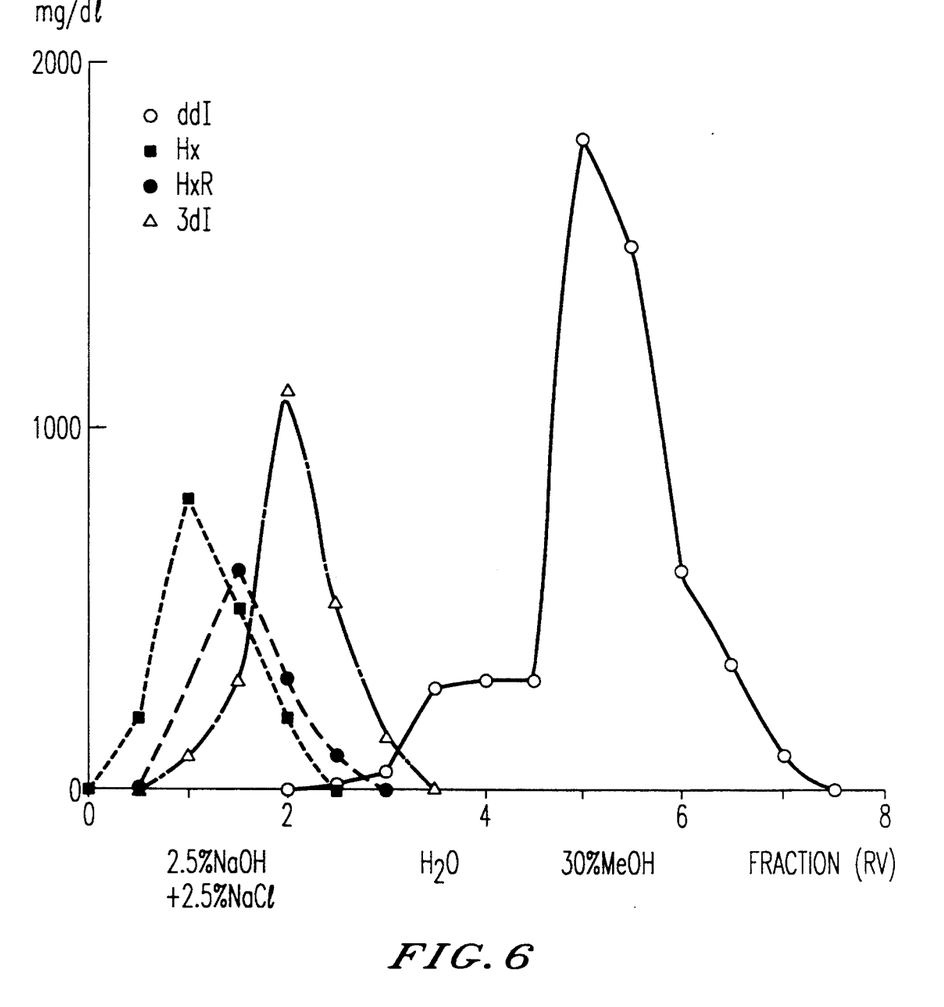
FIG. 6 shows an elution curve in Example 8.

NaOH and NaCl were added to the solution of composition G obtained in Example 5, Synthesis (d) to form an aqueous solution so as to give a 2.5% concentration of each of NaOH and NaCl. When the resulting solution was fed to a column packed with the "SP-207" resin for adsorption (30 g/l—resin concentration), the impurities Hx, HxR and 3dI were eluted rapidly, while the ddI wasn't. After the elution of the impurities, the eluent was replaced with water (1 RV) and further with 30% MeOH (Refer to FIG. 6).

As a result, a ddI elution fraction of high purity could be recovered in high yield (Refer to Table 13) and with a total liquid amount of 8 RV. The results were substantially the same as those in Example 7.

EXAMPLE 9

NaOH was added to the solution of Composition E obtained in Example 5, Synthesis (b), to prepare an aqueous solution having a 5% concentration of NaOH. When the solution was fed to a column packed with the "SP-207" resin for adsorption (30 g/l—resin concentration), the impurities Hx and HxR were eluted rapidly, while the ddI wasn't. After the elution of the impurities, the eluent was replaced with water (1 RV) and further with 30% MeOH.

As a result, a ddI elution fraction of high purity could be recovered in high yield (Refer to Table 13) and with a total liquid amount of 7 RV.

EXAMPLE 10

NaOH was added to the solution of Composition F obtained in Example 5, Synthesis (c), to prepare an aqueous solution having 5% concentration of NaOH. When the resulting solution was fed to a column packed with the "SP-207" resin for adsorption (30 g/l resin concentration), the impurities Hx and HxR were eluted rapidly, while the ddI wasn't. After the elution of the impurities, the eluent was replaced with water (1 RV) and further with 30% MeOH. As a result, a ddI elution fraction having high purity could be recovered in high yield (Refer to Table 13) and with a total liquid amount of 7 RV. The foregoing results are collectively shown in Table 13 below.

TABLE 13

|  |  | Purity at 90% recovery (%) | Yield (%) upon obtaining fraction of purity > 99% |
|---|---|---|---|
| Comparative Example 1 | ddA pH 10 | 80 | 50 |
| Comparative Example 2 | ddI pH 8 | 75 | 35 |
| Example 2 | ddA 5% NaOH | 98 | 88 |
| Example 3 | ddI 5% NaOH | 99 | 95 |
| Example 4 | ddI NaOH & NaCl | 99 | 95 |
| Example 5 | ddI 5% NaOH | 99 | 96 |
| Example 6 | ddI 5% NaOH | 99 | 97 |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method of purifying 2',3'-dideoxyadenosine, which comprises:
   extracting the 2',3'-dideoxyadenosine with an organic solvent selected from the group consisting of alcohols, acetonitrile, carboxylic acid esters, hydrocarbons, ethers, dichloroethane and ketones from a basic aqueous solution having a pH of not less than 13 of a crude 2',3'-dideoxyadenosine product containing 3'-deoxyadenosine.

2. A method of purifying a 2',3'-dideoxyadenosine, which comprises:
   crystallizing the 2',3'-dideoxyadenosine from a basic aqueous solution having a pH of not less than 13 of a crude 2',3'-dideoxyadenosine product containing 3'-deoxyadenosine.

3. The purification method of claim 1 or 2, wherein said organic solvent is an alcohol.

4. A method of purifying a 2',3'-dideoxynucleoside derivative, which comprises:
   bringing a basic aqueous solution having a pH of not less than 11 of a crude 2',3'-dideoxynucleoside product containing a 3'-deoxynucleoside derivative into contact with a nonpolar porous resin, thereby adsorbing 2',3'-dideoxynucleoside derivatives on the resin, and then
   desorbing the thus adsorbed derivative from the resin.

5. The purification method of claim 4, wherein said 2',3'-dideoxynucleoside derivative is a member selected from the group consisting of 2',3'-dideoxynucleosides, 2',3'-dideoxy-2',3'-didehydronucleosides, 2',3'-dideoxy-3'-azidonucleosides, 2',3'-dideoxy-2'-fluoronucleosides and 2',3'-dideoxy-3'-fluoronucleosides.

6. The purification method of claim 4, wherein said 2',3'-dideoxynucleoside derivative is 2',3'-dideoxyinosine.

7. The purification method of claim 4, wherein said 2',3'-dideoxynucleoside derivative is 2',3'-dideoxyadenosine.

8. The purification method of any one of claims 4 to 7, wherein the pH of said basic aqueous solution is not less than 12.

* * * * *

UNITED STATES PATENT AND TRADEMARK OFFICE
CERTIFICATE OF CORRECTION

PATENT NO. : 5,451,671
DATED : September 19, 1995
INVENTOR(S) : Hiroshi SHIRAGAMI, et al.

It is certified that error appears in the above-indentified patent and that said Letters Patent is hereby corrected as shown below:

On the title page, Item [*], should read --The term of this patent shall extend beyond the expiration date of Pat. No. 4,962,193.--

Signed and Sealed this

Sixteenth Day of January, 1996

Attest:

BRUCE LEHMAN

*Attesting Officer*     *Commissioner of Patents and Trademarks*